United States Patent
Dorman

(10) Patent No.: US 12,213,740 B2
(45) Date of Patent: Feb. 4, 2025

(54) SYSTEM AND METHOD FOR MEDICAL DEVICE PLACEMENT

(71) Applicant: Circinus Medical Technology LLC, Concord, MA (US)

(72) Inventor: John Dorman, Midland, TX (US)

(73) Assignee: Circinus Medical Technology LLC, Concord, MA (US)

( * ) Notice: Subject to any disclaimer, the term of this patent is extended or adjusted under 35 U.S.C. 154(b) by 14 days.

(21) Appl. No.: 18/350,672

(22) Filed: Jul. 11, 2023

(65) Prior Publication Data

US 2023/0346481 A1 Nov. 2, 2023

Related U.S. Application Data

(63) Continuation of application No. 17/233,301, filed on Apr. 16, 2021, now Pat. No. 11,737,828, which is a (Continued)

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1703* (2013.01); *A61B 17/1707* (2013.01); *A61B 17/1757* (2013.01); *A61B 17/7076* (2013.01); *A61B 34/20* (2016.02); *A61B 90/06* (2016.02); *A61B 17/7001* (2013.01); *A61B 17/7082* (2013.01); *A61B 2034/102* (2016.02);
(Continued)

(58) Field of Classification Search
CPC ..................................................... A61B 34/10
See application file for complete search history.

(56) References Cited

U.S. PATENT DOCUMENTS

| 5,143,076 A | 9/1992 | Hardy et al. |
| 5,603,318 A | 2/1997 | Heilbrun et al. |
| (Continued) | | |

FOREIGN PATENT DOCUMENTS

| CN | 101198958 A | 6/2008 |
| CN | 101528122 A | 9/2009 |
| (Continued) | | |

OTHER PUBLICATIONS

International Pat. Appl. No. PCT PCT/US2021/059965, International Search Report and Written Opinion dated Feb. 3, 2022, 7 pgs.
(Continued)

*Primary Examiner* — Christian A Sevilla
(74) *Attorney, Agent, or Firm* — Foley & Lardner LLP

(57) ABSTRACT

Disclosed herein are device and methods for determining an orientation of an instrument for inserting a medical device. One such method includes simulating an insertion point and an orientation of a simulated surgical hardware installation on a diagnostic representation of the bone, and then using an electronic device to align an instrument for inserting a surgical hardware installation at a desired orientation through an insertion point by indicating when an orientation of the electronic device is within a threshold of the simulated orientation.

21 Claims, 16 Drawing Sheets

Related U.S. Application Data continuation of application No. 16/172,593, filed on Oct. 26, 2018, now Pat. No. 11,000,335, which is a continuation of application No. 15/043,480, filed on Feb. 12, 2016, now Pat. No. 10,123,840.

(60) Provisional application No. 62/145,868, filed on Apr. 10, 2015, provisional application No. 62/116,345, filed on Feb. 13, 2015.

(51) Int. Cl.
  *A61B 17/70* (2006.01)
  *A61B 34/20* (2016.01)
  *A61B 90/00* (2016.01)

(52) U.S. Cl.
  CPC . *A61B 2034/107* (2016.02); *A61B 2034/2048* (2016.02); *A61B 2090/374* (2016.02); *A61B 2090/3762* (2016.02)

(56) References Cited

U.S. PATENT DOCUMENTS

| | | | |
|---|---|---|---|
| 5,824,085 A | 10/1998 | Sahay et al. | |
| 5,880,976 A | 3/1999 | DiGioia, III et al. | |
| 6,129,670 A | 10/2000 | Burdette et al. | |
| 6,139,544 A | 10/2000 | Mikus et al. | |
| 6,246,474 B1 | 6/2001 | Cerni et al. | |
| 6,511,236 B1 | 1/2003 | Webjorn et al. | |
| 6,638,281 B2 | 10/2003 | Gorek | |
| RE40,176 E | 3/2008 | Peshkin et al. | |
| 7,611,522 B2 | 11/2009 | Gorek | |
| 8,086,077 B2 | 12/2011 | Eichhorn | |
| 8,442,621 B2 * | 5/2013 | Gorek | A61B 90/39 606/97 |
| 9,119,572 B2 | 9/2015 | Gorek et al. | |
| 9,585,700 B2 | 3/2017 | Wehrle et al. | |
| 10,064,687 B2 | 9/2018 | Haimerl et al. | |
| 10,123,840 B2 | 11/2018 | Dorman | |
| 10,342,619 B2 | 7/2019 | Bracke et al. | |
| 10,561,466 B2 | 2/2020 | Hedblom et al. | |
| 10,602,114 B2 | 3/2020 | Casas | |
| 10,864,023 B2 | 12/2020 | Pak et al. | |
| 11,000,335 B2 | 5/2021 | Dorman | |
| 11,191,592 B2 | 12/2021 | Gorek et al. | |
| 11,484,381 B2 | 11/2022 | Pak et al. | |
| 11,826,111 B2 | 11/2023 | Mahfouz | |
| 11,832,886 B2 | 12/2023 | Dorman | |
| 2002/0035323 A1 | 3/2002 | Saha et al. | |
| 2002/0077540 A1 * | 6/2002 | Kienzle, III | A61B 17/1703 606/130 |
| 2002/0120252 A1 | 8/2002 | Brock et al. | |
| 2002/0140694 A1 | 10/2002 | Sauer et al. | |
| 2003/0181919 A1 | 9/2003 | Gorek | |
| 2003/0199882 A1 | 10/2003 | Gorek | |
| 2003/0236548 A1 | 12/2003 | Hovanes et al. | |
| 2004/0068187 A1 | 4/2004 | Krause et al. | |
| 2005/0113846 A1 | 5/2005 | Carson | |
| 2006/0004322 A1 | 1/2006 | Uesugi et al. | |
| 2007/0276397 A1 | 11/2007 | Tacheco | |
| 2008/0057889 A1 | 3/2008 | Jan | |
| 2008/0086160 A1 | 4/2008 | Mastri et al. | |
| 2008/0200927 A1 | 8/2008 | Hartmann et al. | |
| 2009/0157083 A1 | 6/2009 | Park et al. | |
| 2009/0163901 A1 | 6/2009 | Fisher et al. | |
| 2009/0270868 A1 | 10/2009 | Park et al. | |
| 2009/0292201 A1 | 11/2009 | Kruecker | |
| 2009/0292279 A1 | 11/2009 | Bliweis et al. | |
| 2009/0311655 A1 | 12/2009 | Karkanias et al. | |
| 2010/0100081 A1 | 4/2010 | Tuma et al. | |
| 2010/0153081 A1 | 6/2010 | Bellettre et al. | |
| 2010/0198402 A1 | 8/2010 | Greer et al. | |
| 2010/0210939 A1 | 8/2010 | Hartmann et al. | |
| 2010/0274256 A1 | 10/2010 | Ritchey et al. | |
| 2011/0098721 A1 | 4/2011 | Tran et al. | |
| 2011/0214279 A1 | 9/2011 | Park et al. | |
| 2011/0268248 A1 | 11/2011 | Simon et al. | |
| 2012/0116203 A1 | 5/2012 | Vancraen et al. | |
| 2012/0150243 A9 | 6/2012 | Crawford et al. | |
| 2012/0232834 A1 | 9/2012 | Roche et al. | |
| 2012/0319859 A1 | 12/2012 | Taub et al. | |
| 2013/0085344 A1 | 4/2013 | Merkl et al. | |
| 2013/0095855 A1 | 4/2013 | Bort | |
| 2013/0114866 A1 | 5/2013 | Kasodekar et al. | |
| 2013/0245461 A1 | 9/2013 | Maier-Hein et al. | |
| 2013/0253599 A1 | 9/2013 | Gorek et al. | |
| 2014/0148808 A1 | 5/2014 | Inkpen et al. | |
| 2015/0010220 A1 | 1/2015 | Teichman et al. | |
| 2016/0022374 A1 | 1/2016 | Haider et al. | |
| 2016/0106202 A1 | 4/2016 | Ford | |
| 2016/0235481 A1 | 8/2016 | Dorman | |
| 2016/0250040 A1 | 9/2016 | Hermle et al. | |
| 2016/0324580 A1 | 11/2016 | Esterberg | |
| 2016/0373647 A1 | 12/2016 | Garcia Morate et al. | |
| 2017/0007328 A1 | 1/2017 | Cattin et al. | |
| 2017/0027651 A1 | 2/2017 | Esterberg | |
| 2017/0035517 A1 | 2/2017 | Geri et al. | |
| 2017/0071673 A1 | 3/2017 | Ferro et al. | |
| 2017/0135706 A1 | 5/2017 | Frey et al. | |
| 2017/0172696 A1 | 6/2017 | Saget et al. | |
| 2017/0202633 A1 | 7/2017 | Liu | |
| 2017/0221244 A1 | 8/2017 | Hiraga et al. | |
| 2017/0245947 A1 | 8/2017 | Bozung et al. | |
| 2017/0333134 A1 | 11/2017 | Wollowick et al. | |
| 2018/0000380 A1 | 1/2018 | Stein et al. | |
| 2018/0008358 A1 | 1/2018 | Kostrzewski et al. | |
| 2018/0140362 A1 | 5/2018 | Cal et al. | |
| 2018/0303559 A1 | 10/2018 | Shepherd et al. | |
| 2018/0310956 A1 | 11/2018 | Polster | |
| 2019/0029757 A1 | 1/2019 | Roh et al. | |
| 2019/0046278 A1 | 2/2019 | Steinle et al. | |
| 2019/0060000 A1 | 2/2019 | Dorman | |
| 2019/0090959 A1 | 3/2019 | Haider et al. | |
| 2019/0223962 A1 | 7/2019 | Roldan et al. | |
| 2019/0254754 A1 | 8/2019 | Johnson et al. | |
| 2019/0336179 A1 | 11/2019 | Pak et al. | |
| 2019/0357809 A1 | 11/2019 | Borja | |
| 2019/0388173 A1 | 12/2019 | Pak et al. | |
| 2020/0051274 A1 | 2/2020 | Siemionow et al. | |
| 2020/0111213 A1 | 4/2020 | Chacon et al. | |
| 2020/0197191 A1 | 6/2020 | Akhlaghpour et al. | |
| 2020/0229869 A1 | 7/2020 | Dorman | |
| 2020/0305985 A1 | 10/2020 | Tolkowsky | |
| 2021/0100536 A1 | 4/2021 | Spindle | |
| 2021/0186617 A1 | 6/2021 | Gorek et al. | |
| 2021/0228279 A1 | 7/2021 | Dorman | |
| 2022/0192756 A1 | 6/2022 | Dorman | |
| 2022/0201199 A1 | 6/2022 | Dorman | |
| 2022/0237817 A1 | 7/2022 | Dorman | |
| 2022/0241018 A1 | 8/2022 | Dorman | |
| 2022/0351410 A1 | 11/2022 | Siemionow et al. | |
| 2023/0036038 A1 | 2/2023 | Finley et al. | |
| 2023/0131831 A1 | 4/2023 | Dorman | |
| 2023/0172631 A1 | 6/2023 | Richter et al. | |

FOREIGN PATENT DOCUMENTS

| | | |
|---|---|---|
| CN | 101721231 A | 6/2010 |
| CN | 101984931 A | 3/2011 |
| CN | 103519895 A | 1/2014 |
| EP | 2 901 957 A1 | 8/2015 |
| KR | 101478522 B1 | 1/2015 |
| KR | 101901521 B1 | 9/2018 |
| WO | WO-2013/020026 | 2/2013 |
| WO | WO-2014/025305 A1 | 2/2014 |
| WO | WO-2014/063181 A1 | 5/2014 |
| WO | WO-2015/168781 | 11/2015 |
| WO | WO-2016/007936 | 1/2016 |
| WO | WO-2016/131016 A2 | 8/2016 |
| WO | WO-2017/167799 A1 | 10/2017 |
| WO | WO-2018/200767 A1 | 11/2018 |
| WO | WO-2019/036524 A1 | 2/2019 |
| WO | WO-2020/214645 A1 | 10/2020 |

(56) References Cited

FOREIGN PATENT DOCUMENTS

| WO | WO-2020/214744 A1 | 10/2020 |
| WO | WO-2020/216934 A1 | 10/2020 |
| WO | WO-2022/109185 A1 | 5/2022 |

OTHER PUBLICATIONS

International Pat. Appl. No. PCT/US2020/028220, International Search Report and Written Opinion, dated Aug. 14, 2020, 22 pgs.
International Pat. Appl. No. PCT/US2020/028375, International Search Report and Written Opinion dated Jul. 21, 2020, 10 pgs.
International Patent Appl. No. PCT/US2022/022204, International Search Report and Written Opinion dated Jun. 10, 2022, 18 pgs.
International Preliminary Report on Patentability for PCT Application No. PCT/US16/17897 dated Aug. 15, 2017, 9 pages.
International Preliminary Report on Patentability, International Patent Appl. No. PCT/US2018/046786, dated Feb. 27, 2020, 7 pages.
International Search Report and Written Opinion in corresponding international application No. PCT/US2016/017897, mailed Aug. 24, 2016, 13 pages.
International Search Report and Written Opinion in PCT/US18/46786, dated Dec. 13, 2018, 10 pgs.
International Search Report and Written Opinion issued in PCT/US2022/014988 Dtd Apr. 6, 2022, 17 pages.
International Search Report and Written Opinion on PCT/US2022/047306 Dated Mar. 28, 2023.
Julian Horsey, "Ozaki iCoat Finger Case Makes Draw Something Even More Fun", Apr. 20, 2012, pp. 1-11, XP093028330, Retrieved from the Internet: URL:https://www.geeky-gadgets.com/ozaki-icoat-finger-case-makes-draw-someting-even-more-fun-20-04-2012/ [retrieved on Mar. 2, 2023].
Merloz et al., "Pedicle Screw Placement Using Image Guided Techniques." Clinical Orthopaedics and Related Research, No. 354, pp. 39-48, 1998, entire document [online] URL=<https://journals.lww.com/clinorthop/Fulltext/1998/09000/Pedicle_Screw_Placement_Using_Image_Guided.6.aspx>.
International Search Report and Written Opinion for International Patent Application PCT/US2022/024683 dated Jun. 21, 2022.
U.S. Appl. No. 16/639,107, filed Feb. 13, 2020, System and Method Using Augmented Reality With Shape Alignment for Medical Device Placement.
U.S. Appl. No. 17/604,359, filed Oct. 15, 2021, Attachment Apparatus to Secure a Medical Alignment Device to Align a Tool.
U.S. Appl. No. 17/604,362, filed Oct. 15, 2021, Orientation Calibration System for Image Capture.
U.S. Appl. No. 17/530,311, filed Nov. 18, 2021, Systems and Methods for Artificial Intelligence Based Image Analysis for Placement of Surgical Appliance.
U.S. Appl. No. 17/591,478, filed Feb. 2, 2022, Systems and Methods for Simulating Three-Dimensional Orientations of Surgical Hardware Devices About an Insertion Point of an Anatomy.
U.S. Appl. No. 17/970,378, filed Oct. 20, 2022, Attachment Apparatus to Secure a Medical Alignment Device to Align a Tool.
U.S. Appl. No. 18/554,969, filed Oct. 11, 2023, System and Method for Lidar-Based Anatomical Mapping.
Harrison, Peter, Simpler Line Follower Sensors, Micromouse Online, Apr. 15, 2011, https://web.archive.org/web/20120422001123 /https://micromouseonline.com/2011/04/15/simpler-line-follower-sensors/. (Year: 2011), 3 pgs.
NumPy—Data Types, tutorialspoint, https://web.archive.org/web/20181126133733/https://www.tutorialspoint.com/numpy/numpy_data_type.htm. 2018 (Year: 2018), 8 pgs.
Crescendo CR-30 phone holder. Amazon datasheet [online]. Crescendo, first available on Nov. 18, 2017. [Retrieved on Jun. 13, 2024]; Retrieved from the Internet. <URL: https://a.co/d/fyEOcbM>.
U.S. Appl. No. 16/639,107, filed Feb. 13, 2020, System and Method Using Augmented Reality With Shape Alignment For Medical Device Placement in Bone.
U.S. Appl. No. 17/233,301, filed Apr. 16, 2021, System and Method for Medical Device Placement.
U.S. Appl. No. 17/591,478, filed Feb. 2, 2022, Systems and Methods for Simulating Three-Dimmensional Orientations of Surgical Hardware Devices About an Insertion Point of an Anatomy.
U.S. Appl. No. 18/513,155, filed Nov. 17, 2023, Circinus Medical Technology LLC.
U.S. Appl. No. 18/553,025, filed Sep. 28, 2023, Circinus Medical Technology LLC.
U.S. Appl. No. 18/554,969, filed Oct. 11, 2023, Circinus Medical Technology LLC.
A. Elmi-Terander et al., "Surgical Navigation Technology Based on Augmented Reality and Integrated 3D Intraoperative Imaging: A Spine Cadaveric Feasibility and Accuracy Study", Spine 41.21 (2016): E1303-E1311.
M. Herold, "Using Deep Convolutional Networks to Regress a C-arm's Position from a single X-ray Image", Diss. 2020.
G. Wells et al., "Vision-based robot positioning using neural networks", Image and Vision Computing, 14 (1996) 715-732.

* cited by examiner

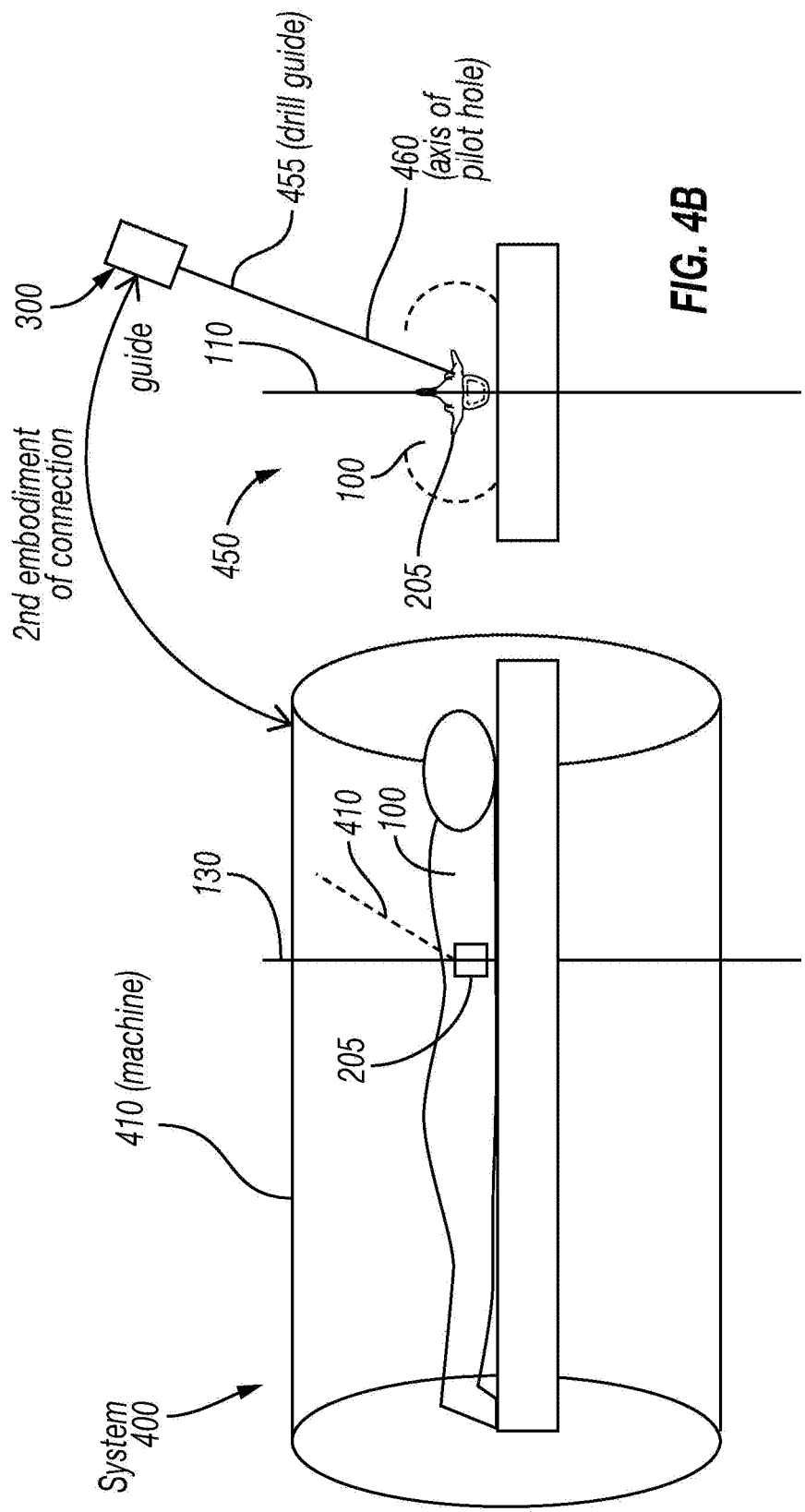

SYSTEM AND METHOD FOR MEDICAL DEVICE PLACEMENT

RELATED APPLICATIONS

This continuation application claims the benefit and priority of previously filed provisional patent application U.S. App. No. 62/145,868, filed Apr. 10, 2015 and titled "SYSTEM AND METHOD FOR PEDICLE SCREW PLACEMENT IN VERTEBRA," of previously filed provisional patent application U.S. Appl. No. 62/116,345, filed Feb. 13, 2015 and titled "SYSTEM AND METHOD FOR PEDICLE SCREW PLACEMENT IN VERTEBRA," and of previously filed nonprovisional patent application U.S. application Ser. No. 15/043,480, filed Feb. 12, 2016 and titled "SYSTEM AND METHOD FOR MEDICAL DEVICE PLACEMENT IN BONE," and of previously filed nonprovisional patent application U.S. application Ser. No. 16/172,593, filed Oct. 26, 2018 and titled "SYSTEM AND METHOD FOR MEDICAL DEVICE PLACEMENT IN BONE," and of previously filed nonprovisional patent application U.S. application Ser. No. 17/233,301, filed Apr. 16, 2021 and titled "SYSTEM AND METHOD FOR MEDICAL PLACEMENT," and the contents of all are hereby incorporated by reference in their entirety.

TECHNICAL FIELD

This disclosure generally relates to medical systems. More specifically, this disclosure relates to an electronic device that generates output which facilitates the aligning and orientation of surgical equipment for use in inserting a medical device in a bone. In one implementation, the surgical equipment is used to create a pilot hole in a vertebra for receiving a pedicle screw at a precise orientation, such as a transverse angle, sagittal angle, or any other angle.

BACKGROUND

Patients who undergo certain procedures, such as a spinal fusion, may have pedicle screws placed into their vertebrae. The pedicle screws are typically implanted into the vertebrae through the pedicles of the vertebrae. Once a pilot hole is created through the cortex of the bone, a probe is used to create the path through which the pedicle screw will be placed into the vertebrae. Placing the pedicle screw at the correct angle helps to assure a mechanically sound construct and to avoid injury to surrounding structures such as the spinal cord, nerve roots, and blood vessels. The orientation of the screw can be described in two planes: (1) the transverse plane, which is parallel to the ground if the person is standing upright, and (2) the sagittal plane, which divides a person into left and right halves.

To assist surgeons to properly place and orient a pedicle screw in a vertebra, a variety of machines have been used. However, these machines are typically costly and bulky, thereby reducing the number of available surgical suites that have suitable equipment for use in assisting a surgeon with properly placing and orienting a pedicle screw. Therefore, further developments in medical technology are needed so as to enable physically smaller, cost effective devices that provide the desired level of assistance to surgeons.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method disclosed herein includes simulating an insertion point and an orientation of a simulated surgical hardware installation on a diagnostic representation of the bone, and then using an electronic device to align an instrument for inserting a surgical hardware installation at a desired orientation through an insertion point of the bone by indicating when an orientation of the electronic device is within a threshold of the simulated orientation.

An apparatus disclosed herein is for determining orientation of an instrument for inserting a medical device in a bone. The apparatus includes an electronic device having an orientation sensor, and a processor. The processor is configured to simulate insertion of the medical device in an image of the bone to determine a desired insertion angle of the medical device relative to a plane of the bone, determine an orientation of the electronic device relative to the plane using the orientation sensor, and output a notification when the orientation of the electronic device is such that the electronic device is positioned adjacent the desired angle of the medical device relative to the plane.

Another method aspect is directed to a method for verifying an insertion angle of an instrument for determining a correct angle for a pedicle screw in a vertebra. The method includes aligning an axis of an apparatus with at least one of a sagittal plane, transverse plane, and coronal plane of the vertebra in a representation thereof. The method also includes capturing an image of the representation of the vertebra, and generating an angle-indicative line on a display, wherein the angle-indicative line adjusts in response to rotation and orientation of the apparatus and provides a notification when the apparatus is at the correct angle, the correct angle being a desired angle between the axis of the apparatus and at least one of the sagittal plane, transverse plane, and coronal plane.

A further aspect is directed to a system for indicating an insertion sagittal angle of a tract for receiving a pedicle screw in a vertebra. The system includes an image acquisition unit, an orientation sensor, a display, and a processor. The processor is configured to obtain an image of a cross sectional view in a transverse plane of the vertebra, using the image acquisition unit, and measure orientation of the system and calibrate the orientation to align with a sagittal plane, transverse plane, or coronal plane of the vertebra. The processor is further configured to receive definitions of an insertion sagittal angle, transverse angle, or coronal angle of the tract and an initial position thereof relative to the vertebra, and generate an angle-indicative line on the display, wherein the angle-indicative line rotates in response to rotation of the system, and provides a notification when at least a portion of the system approximately forms the insertion sagittal angle, transverse angle, or coronal angle between an axis of the apparatus and the sagittal plane, transverse plane, or coronal plane of the vertebrae.

BRIEF DESCRIPTION OF THE DRAWINGS

For a more complete understanding of various embodiments of the present invention and the advantages thereof, reference is now made to the following brief description, taken in connection with the accompanying drawings, appendices, and detailed description, wherein like reference numerals represent like parts, and in which:

FIG. 4A illustrates a schematic side view of a medical operation system used in some embodiments for defining the sagittal angle of a vertebra;

FIG. 4B illustrates a schematic front view of a medical operation system used in some embodiments for defining the sagittal angle of a vertebra;

FIGS. 6A-6D illustrate example user interfaces for a computer-implemented program to perform the methods shown in FIGS. 5A-5D, wherein FIG. 6A illustrates an interface for selecting vertebra of a patient, FIG. 6B illustrates aligning the longitudinal axis of the apparatus with the sagittal plane, FIG. 6C illustrates defining a pedicle screw's position and its sagittal angle, and FIG. 6D illustrates generating an angle-indicative line for showing the angle between the longitudinal axis of the apparatus and the sagittal plane;

DETAILED DESCRIPTION

In the following detailed description and the attached drawings and appendices, numerous specific details are set forth to provide a thorough understanding of the present disclosure. However, those skilled in the art will appreciate that the present disclosure may be practiced, in some instances, without such specific details. In other instances, well-known elements have been illustrated in schematic or block diagram form in order not to obscure the present disclosure in unnecessary detail. Additionally, for the most part, specific details, and the like, have been omitted inasmuch as such details are not considered necessary to obtain a complete understanding of the present disclosure, and are considered to be within the understanding of persons of ordinary skill in the relevant art.

It is further noted that, unless indicated otherwise, all functions described herein may be performed in hardware or as software instructions for enabling a computer, radio or other device to perform predetermined operations, where the software instructions are embodied on a computer readable storage medium, such as RAM, a hard drive, flash memory or other type of computer readable storage medium known to a person of ordinary skill in the art. In certain embodiments, the predetermined operations of the computer, radio or other device are performed by a processor such as a computer or an electronic data processor in accordance with code such as computer program code, software, firmware, and, in some embodiments, integrated circuitry that is coded to perform such functions. Furthermore, it should be understood that various operations described herein as being performed by a user may be operations manually performed by the user, or may be automated processes performed either with or without instruction provided by the user.

This disclosure describes a system and computer-implemented method for indicating an angle formed between a guiding direction for drilling a pilot hole (also referred to herein as a tract) for receiving a pedicle screw and a reference plane such as, for example, the sagittal plane.

The disclosed system and method may be implemented to guide the insertion of pedicle screws at a desired angle. The desired angle may be a transverse angle, sagittal angle, or any other angle. This process may include, in some embodiments, the creation of pilot holes.

Figure 1:
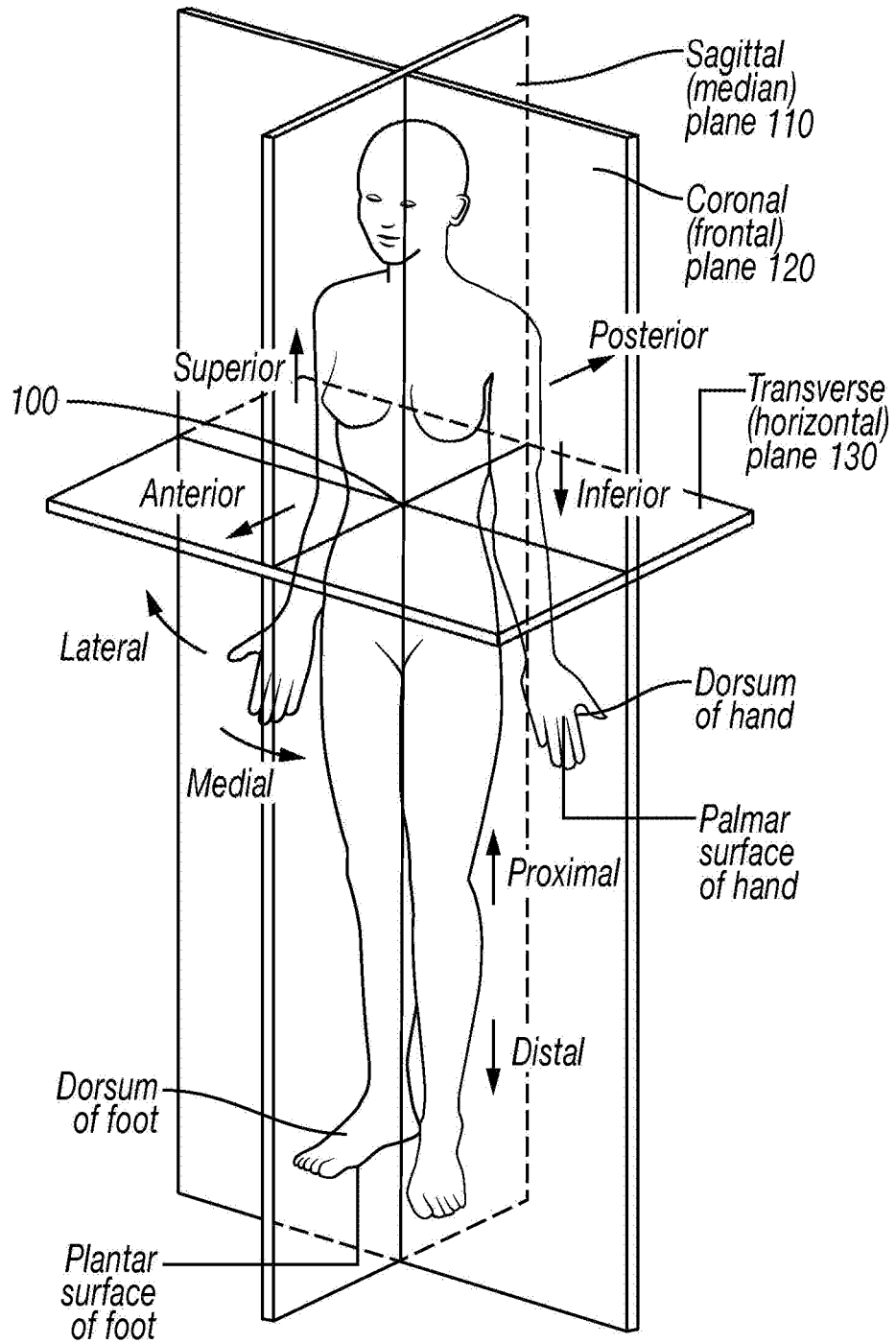
FIG. 1 illustrates definitions of a sagittal plane, a frontal plane, and a transverse plane relative to a patient's body.

FIG. 1 illustrates a sagittal or median plane 110, a coronal or frontal plane 120, and a transverse or horizontal plane 130 relative to a patient's body part 100 located at the intersection of the sagittal plane 110, coronal plane 120, and transverse plane 130. Each plane is orthogonal to each other. When discussing a vertebra (or other body parts) in the following disclosure, reference is made to the sagittal plane, coronal plane, and transverse plane. It should be understood that, when these planes are mentioned, they are not intended as a reference to the specific sagittal, coronal, and transverse planes illustrated in FIG. 1, but rather, are intended as a reference to illustrate an orientation or location relative to the specific vertebra being discussed.

Figure 2A:
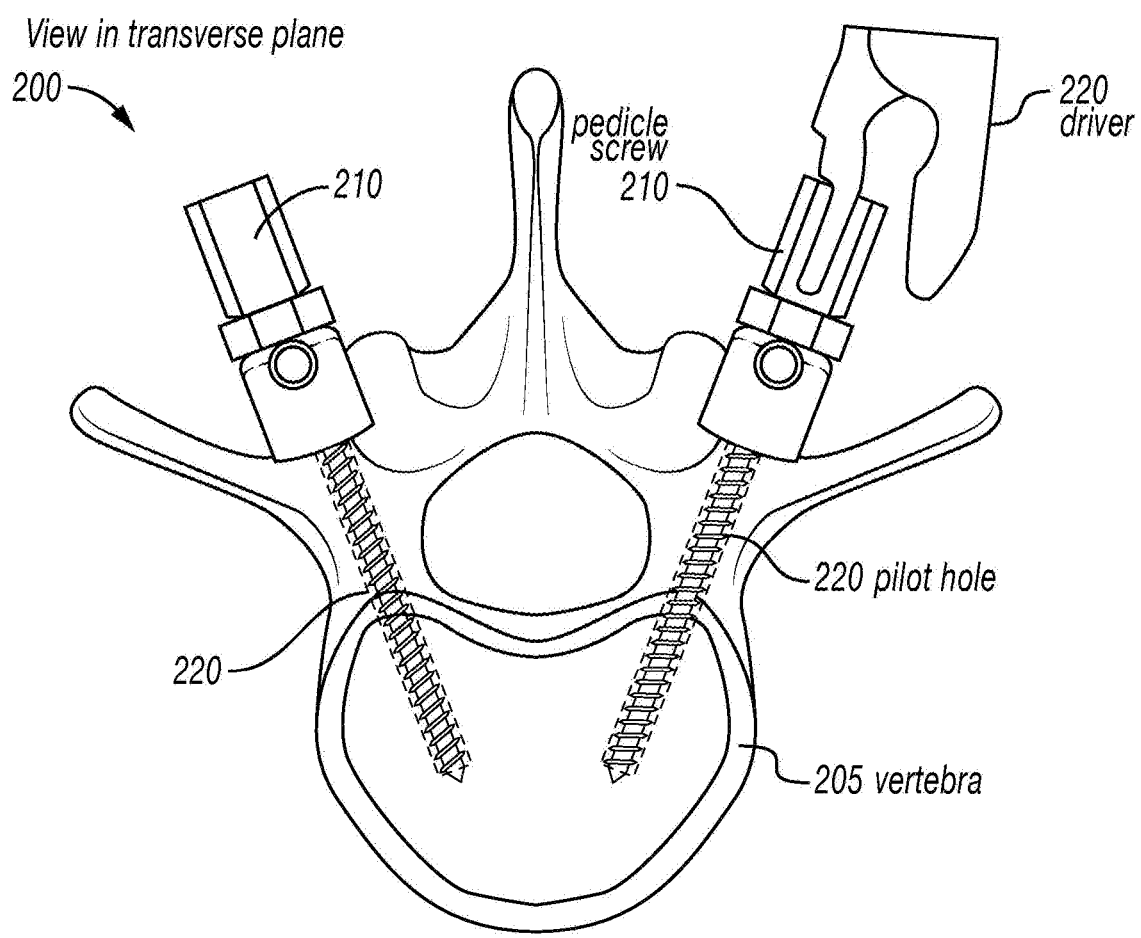
FIG. 2A illustrates a cross-sectional view of a vertebra having pedicle screws installed in respective pilot holes.
Figure 2B:
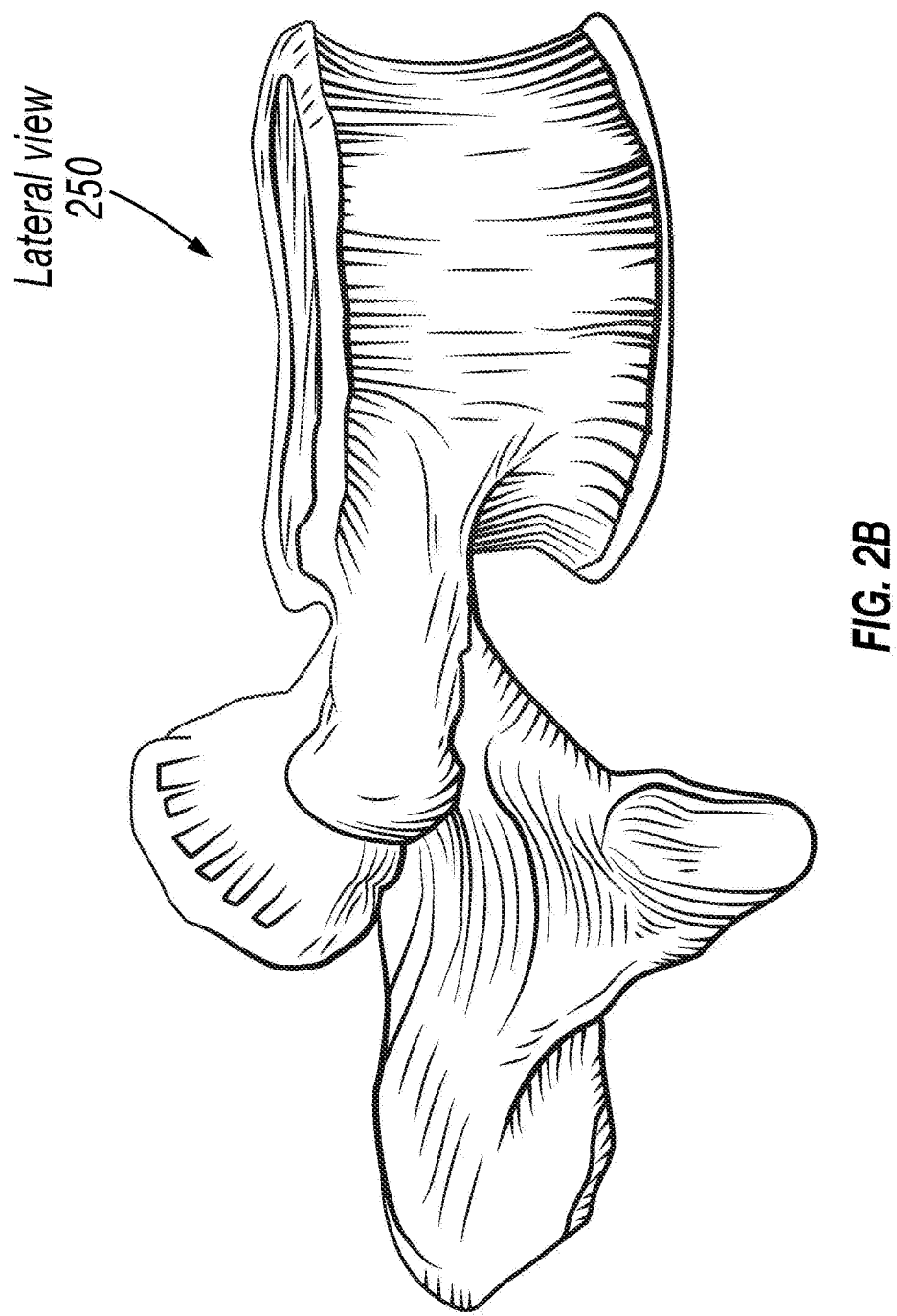
FIG. 2B illustrates an example lateral view of a vertebra for installing pedicle screws.
Figure 2C:
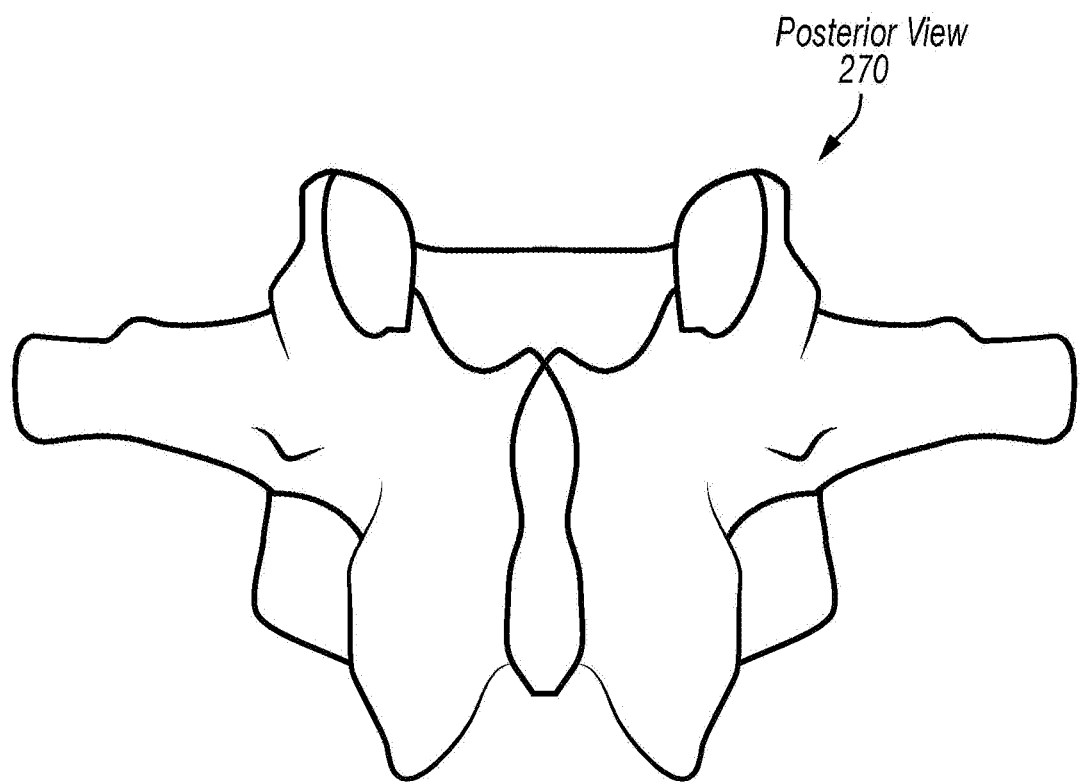
FIG. 2C illustrates an example posterior view of a vertebra for installing pedicle screws.

FIG. 2A illustrates a cross sectional view (i.e., superior view) 200 of a vertebra 205 having pedicle screws 210 installed in respective pilot holes 220. A driver 230 may be used to screw the pedicle screws 210 into the pilot holes 220. FIG. 2B illustrates a lateral view (i.e., side view) 250 of a vertebra, and FIG. 2C illustrates a posterior view 270 of a vertebra. The following discussion focuses on properly creating the pilot holes with a tool guided by the method disclosed.

Figure 3A:
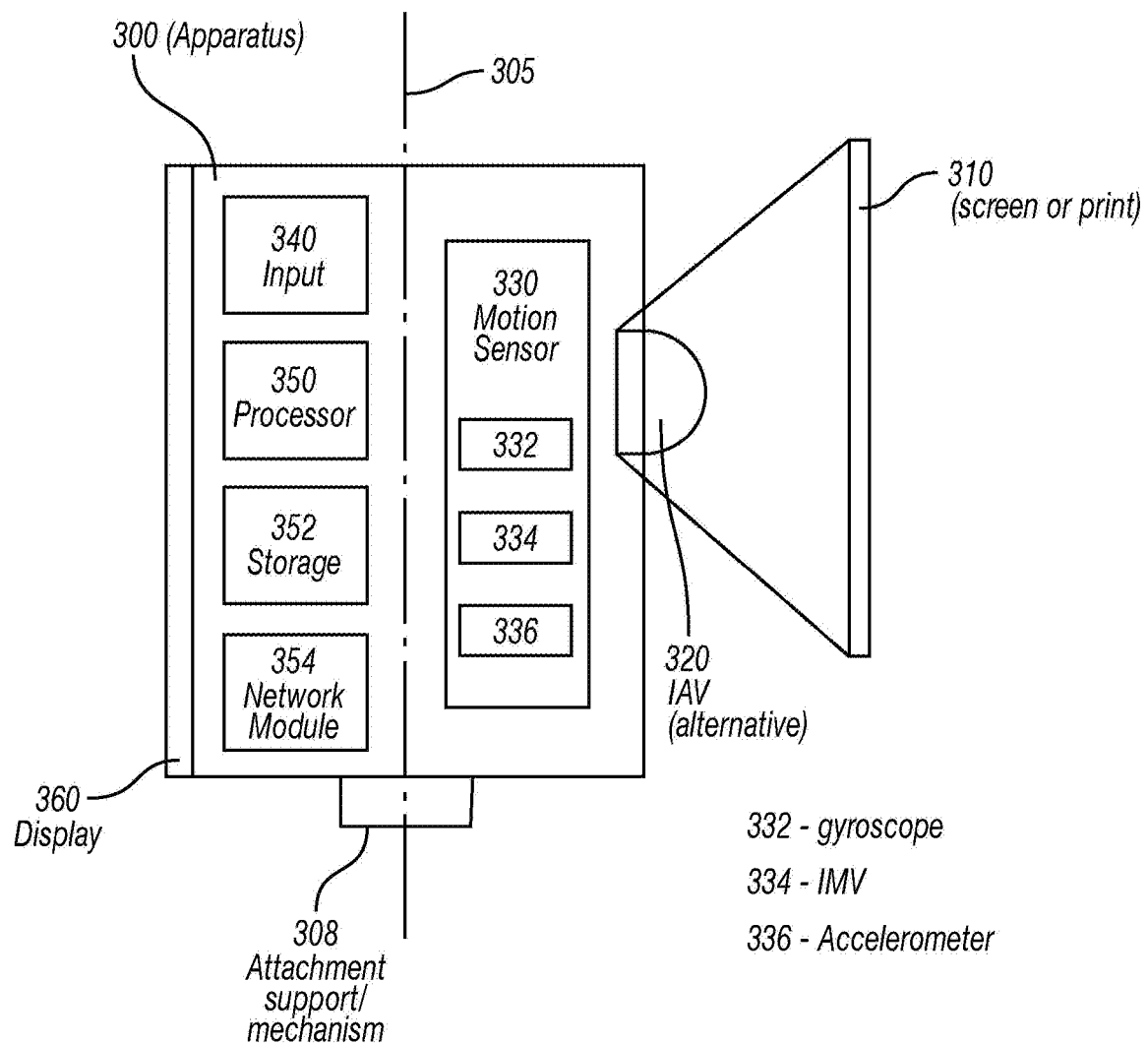
FIG. 3A presents a schematic diagram of an apparatus used in accordance with an embodiment to define and verify a sagittal angle for a pilot hole.

FIG. 3A presents a schematic diagram of an apparatus 300 used to define and verify an angle for a pilot hole, or tract, such as the pilot hole 220 of FIG. 2. The apparatus 300 has an axis 305 (such as, for example, a longitudinal axis) that is used in some embodiments to align the apparatus 300 for image capture. The apparatus 300 includes an image acquisition unit 320 for capturing an image 310 of the vertebra. In some embodiments, the image 310 may be obtained by positioning the apparatus 300 and/or image acquisition unit 320 in parallel with the transverse, sagittal, or coronal plane to obtain an image of the vertebra.

In some embodiments, the image acquisition unit 320 can be a camera having sufficient field of view 360 to properly align the axis 305 of the apparatus 300 with the desired plane. In some embodiments, the axis 305 is representative of a vertical line centered laterally with respect to the image being captured. For example, if the desired image is intended to capture the vertebra from a cross sectional, superior view (e.g., see FIG. 2A), the axis 305 is aligned with the sagittal plane (i.e., the plane that is sagittal to the vertebra) and the image acquisition unit 320 is positioned parallel to the transverse plane to capture the top-down view of the vertebra shown in FIG. 2A. If the desired image is intended to capture the vertebra from a side view (e.g., a lateral image of the vertebra, see FIG. 2B), the axis 305 is aligned with the transverse plane (i.e., the plane that is transverse to the vertebra) and the image acquisition unit 320 is positioned parallel to the sagittal plane. If the desired image is intended to capture the vertebra from a posterior or anterior view (see, for example, FIG. 2C), the axis 305 is aligned with the sagittal plane and the image acquisition unit 320 is positioned parallel to the coronal plane.

In some embodiments, the image 310 may be a processed image, e.g., an image displayed on a screen, a film, or a printed photograph. In other embodiments, the image acquisition unit 320 can directly use an image taken from an external machine (not illustrated), such as a radiograph, computed tomography (CT) scanner, or a magnetic resonance imaging (MRI) machine.

The orientation apparatus 330 is operable to detect changes in movement, orientation and position. In some embodiments, the orientation apparatus 330 includes at least one of a gyroscope 332, an inertial measurement unit 334, and an accelerometer 336. The gyroscope 332 is operable to measure at least one axis of rotation, for example, the axis parallel to the intersection of the sagittal plane and the coronal plane. In other embodiments, the gyroscope 332 includes more than one sensing axes of rotation, such as three axes of rotation, for detecting changes in orientation. The inertial measurement unit 334 can detect changes of position in one or more directions in a cardinal coordinate system. The accelerometer 336 can detect changes of speeds in one or more directions in a cardinal coordinate system. In some embodiments, data from all components of the orientation apparatus 330 are used to calculate the continuous, dynamic changes in orientation and position.

The apparatus 300 further includes, in some embodiments, an input component 340 that is operable to receive user input, and insertion location and the desired angle representing an insertion direction of the pedicle screw. An example illustration of the user input component 340 is presented in accordance with FIGS. 6A-6D. In some embodiments, the input component 340 can include a multi-touch screen, a computer mouse, a keyboard, a touch sensitive pad, or any other input device.

In some embodiments, the apparatus 300 further includes a processor 350. The processor 350 can be any processing unit capable of basic computation and capable of executing a program, software, firmware, or any application commonly known in the art of computer science. As to be explained, the processor 350 is operable to output an angle-indicative line representing the apparatus orientation on the display. In some embodiments, the angle-indicative line provides a notation that the orientation of the apparatus 300 approximately forms the desired angle. The angle-indicative line is not limited to showing sagittal angles, but also angles in different planes, such as, for example, the coronal plane or the transverse plane.

The apparatus 300 may, in some embodiments, further include a memory storage unit 352 and network module 354. The memory storage unit 352 can be a hard drive, random access memory, solid-state memory, flash memory, or any other storage device. Memory storage unit 352 saves data related to at least an operating system, application, and patient profiles. The network module 354 allows the apparatus 300 to communicate with external equipment as well as communication networks.

In some embodiments, the apparatus 300 further includes a display 360. In some embodiments, the display 360 is a liquid crystal display for a multi-touch screen. In some embodiments, the display 360 shows the angle-indicative line to a user and provides a notification when the apparatus is approximately aligned with the predefined desired angle. For example, the notification can include a highlighted line that notifies the user the axis 305 has reached the desired angle, or is within an acceptable range of the desired angle.

Figure 7:
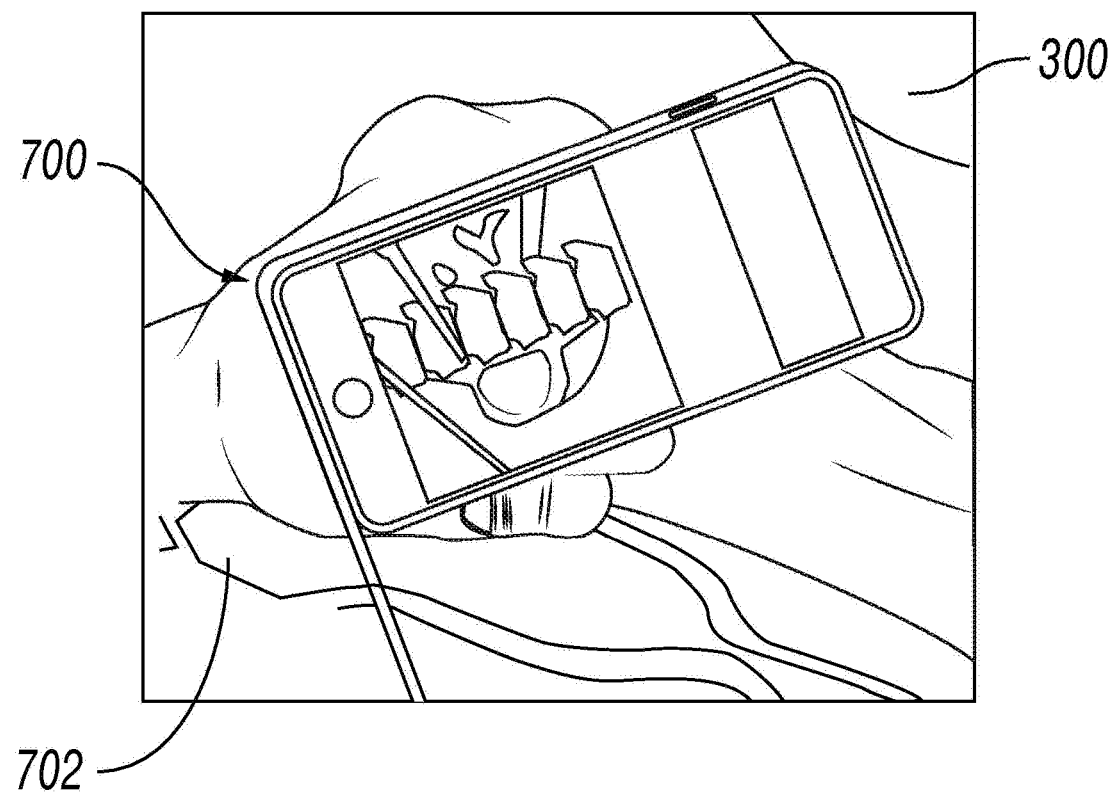
FIG. 7 illustrates an example application of the aligning method presented in FIG. 5B or 5C; and Like elements are indicated with like reference numerals.

Referring briefly to FIG. 7, in some implementations, the apparatus 300 further includes an attachment support or mechanism that allows the apparatus 300 to be attached to medical equipment, for example, for creating the pilot holes as shown in FIG. 7. The attachment mechanism 700 may be comprised of plastic, stainless steel, titanium, or any other material. The attachment mechanism 700 couples the apparatus 300 to the equipment 702 by, for example, providing a casing that is attached to the apparatus 701 and is configured to connect to the equipment 702. In some embodiments, the attachment mechanism 700 may include a magnetic attachment apparatus for coupling the apparatus 300 to the equipment 702. The attachment mechanism 700 allows the apparatus 300 to provide real-time measurement and display of the orientation of the attached medical equipment 702.

Figure 3B:
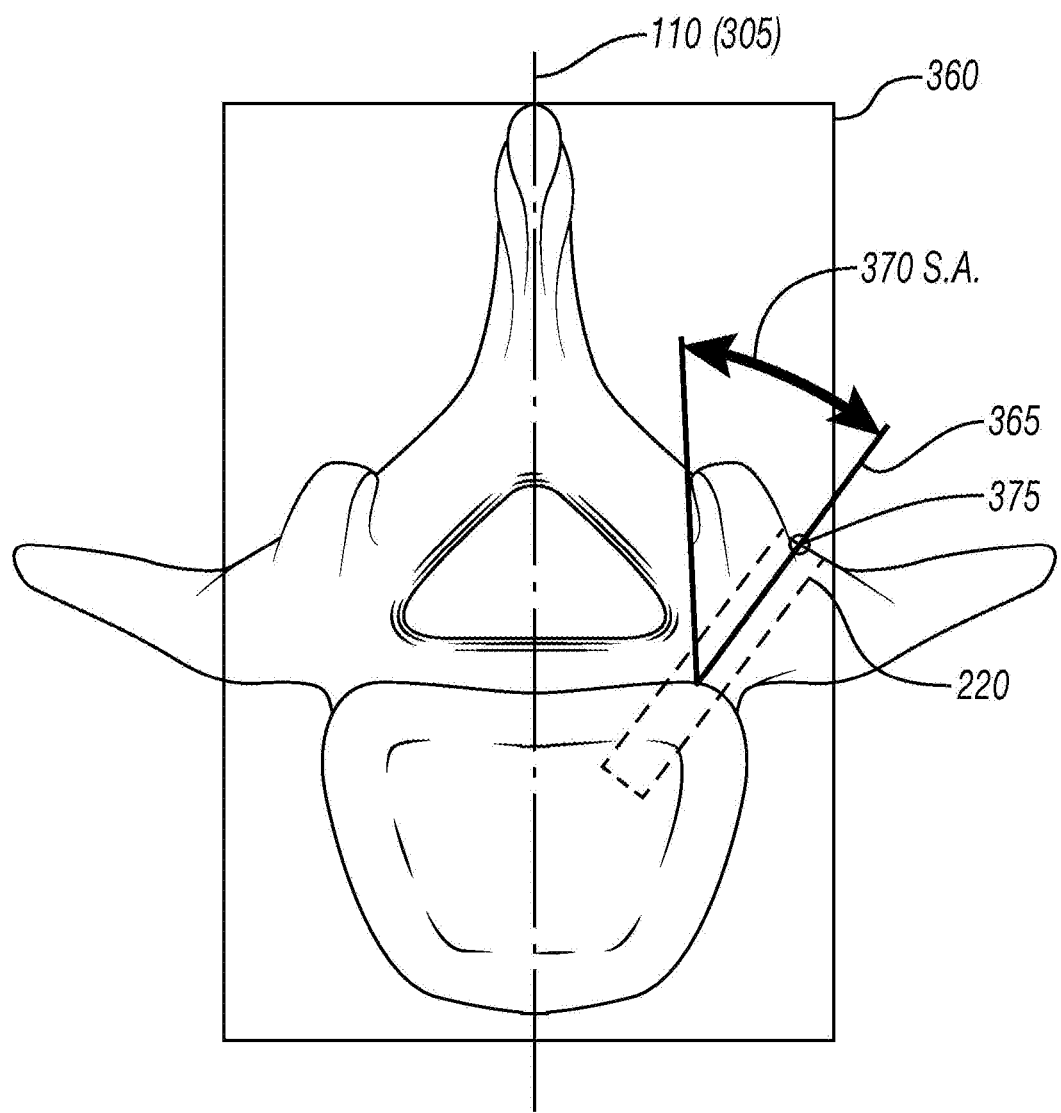
FIG. 3B illustrates a schematic diagram for defining a sagittal angle for a pilot hole in a vertebra.

FIG. 3B illustrates a schematic diagram for defining the sagittal angle 370 for the pilot hole 220 in the vertebra 205. The field of view 360 of the image acquisition unit 320 allows a user to align the axis 305 of the apparatus 300 with the desired plane (e.g., the sagittal plane). In the embodiment shown in FIG. 3B, the sagittal angle 370 is the angle between the central axis 365 of the pilot hole 220 and the sagittal plane.

FIG. 4A illustrates a schematic side view of a medical operation system 400, which may be used in some embodiments for defining the sagittal angle 370 of the vertebra shown in FIGS. 3A and 3B. The medical operation system 400 includes a machine 410 for capturing a cross-sectional view of the vertebra 205. The machine 410 may be, for example, a CT scanner or MRI machine. The patient 108 exits the machine 410 after the image is taken, as shown in FIG. 4B.

FIG. 4B illustrates a schematic front view 450 of the medical operation system 400 taken in the transverse plane for defining the sagittal angle 370 of the vertebra 205. The axis of the pilot hole 460 should to be precisely defined for the drilling guide 455. In some embodiments, the apparatus 300 may be attached to the drilling guide 450 with the attachment mechanism 308. Defining and verifying the sagittal angle 370 may be performed at the apparatus 300, as explained in connection with the method illustrated in FIG. 5B.

Figure 5A:
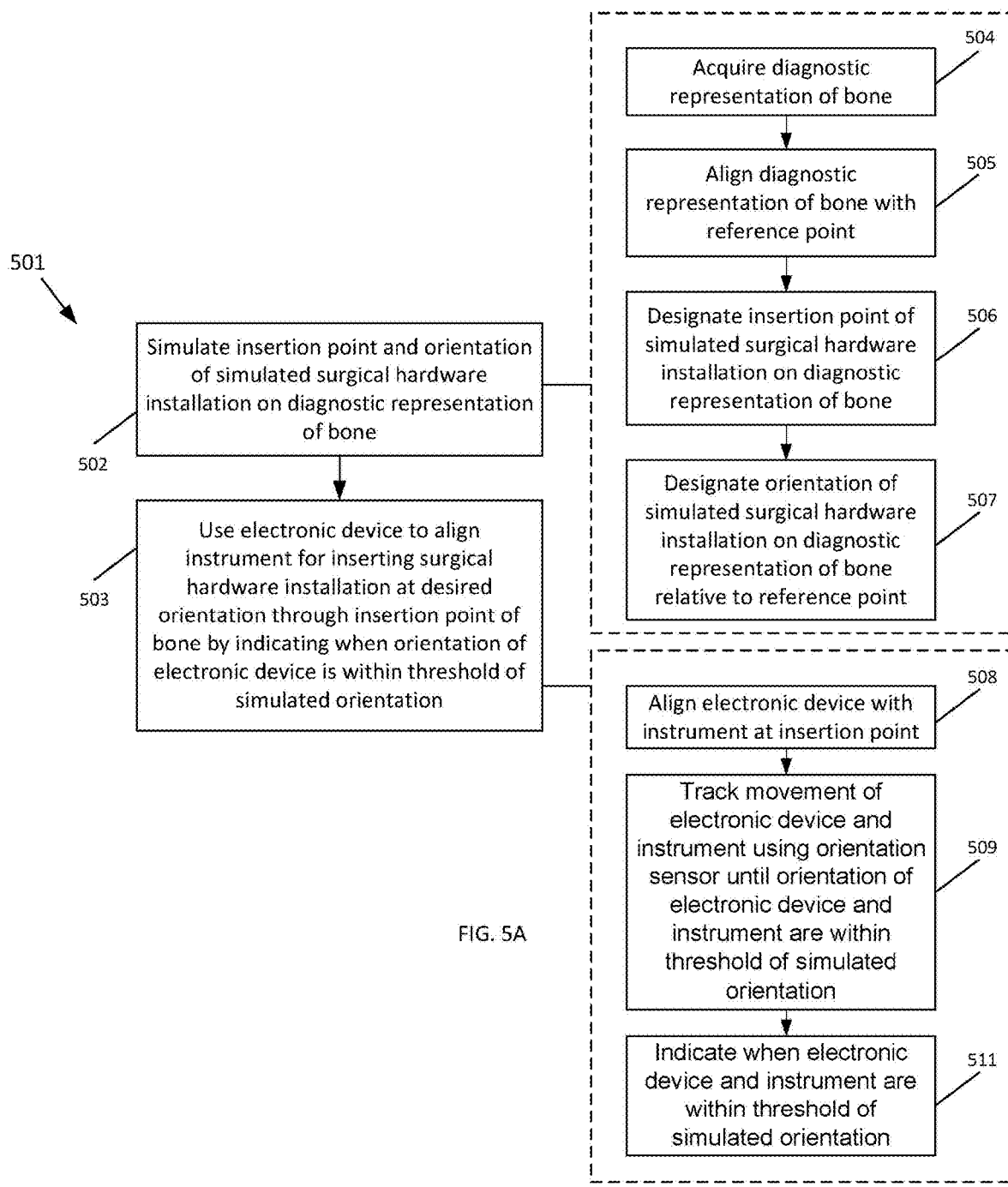
FIG. 5A illustrates an example flow chart for a method of determining an orientation of an instrument for inserting a medical device in a bone, in accordance with one or more embodiments of the present disclosure.

First, however, a method of determining an orientation of an instrument for inserting a medical device in a bone is now described with reference to the flowchart 501 of FIG. 5A.

First an insertion point and an orientation of a simulated surgical hardware installation are simulated on a diagnostic representation of a bone 502. Then, an electronic device is used to align an instrument for inserting a surgical hardware installation at a desired orientation through an insertion point of the bone by indicating when an orientation of the electronic device is within a threshold of the simulated orientation 503.

Simulating the insertion point and the orientation of the simulated surgical hardware installation on the diagnostic representation of the bone includes acquiring the diagnostic representation of the bone 504, aligning the diagnostic representation of the bone with a reference point 505, designating the insertion point of the simulated surgical hardware installation on the diagnostic representation of the bone 506, and designating the orientation of the simulated surgical hardware installation on the diagnostic representation of the bone relative to the reference point 507.

Using the electronic device to align the instrument for inserting the surgical hardware installation at the desired orientation through the insertion point includes aligning the electronic device with the instrument at the insertion point 508, tracking movement of the electronic device and the instrument using an orientation sensor of the electronic device until the orientation of the electronic device and the instrument are within the threshold of the simulated orientation 509, and indicating when the electronic device and the instrument are within the threshold of the simulated orientation 511.

Figure 5B:
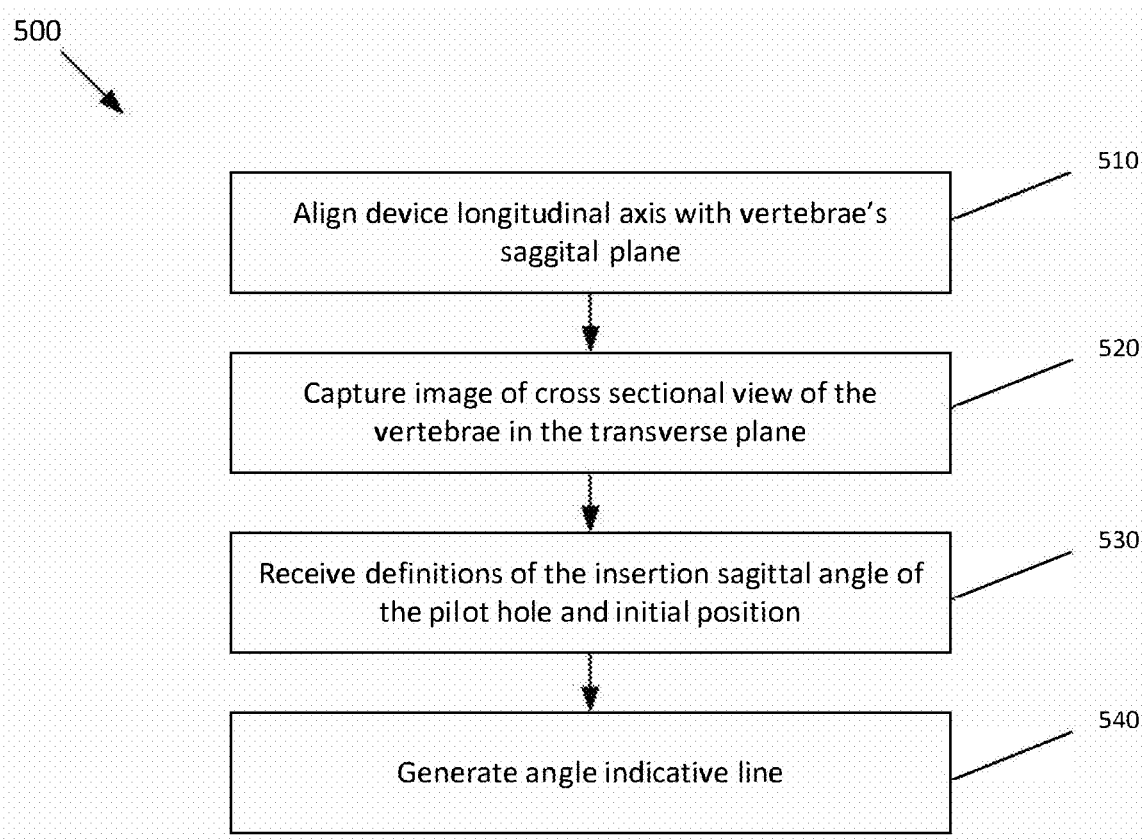
FIGS. 5B, 5C, and 5D illustrate example flow charts for methods for indicating the sagittal angle, transverse angle, and coronal angle, respectively, in accordance with one or more embodiments of the present disclosure.

FIG. 5B illustrates an example flow chart 500 of a method for indicating the sagittal angle 370. The method of the flowchart 500 is for verifying any insertion angle 370 of the pilot hole 220 in the sagittal plane 110 for receiving a pedicle screw 210 in the vertebra 205. At 510, the axis 305 of the apparatus 300 is aligned with the sagittal plane. In some embodiments, a user may hold the apparatus 300 and rotate the apparatus 300 to match a marking indicating the axis 305 with features of the vertebra 205 that indicate the sagittal plane. In some embodiments, the marking may be displayed on the screen as the user aligns the device.

At 520, the image of the cross-sectional view is captured in the transverse plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 530, definitions of the insertion sagittal angle 370 of the pilot hole 220 and the initial position 375 of the pilot hole are provided by a user. This input operation may be performed using various input devices, including a computer mouse, a keyboard, a touchscreen, or the like. In one embodiment, a multi-touch screen (e.g., the display 360) is used for both displaying the image and receiving the definition input from a user. Example illustrations of this input are provided in FIGS. 6A-6D.

At 540, an angle-indicative line is generated by a processor and displayed on the display 360. The angle-indicative line can rotate in response to the apparatus 300 rotation and provides a notification when the apparatus 300 approximately forms the insertion sagittal angle 370 between the apparatus 300 longitudinal axis 305 and the sagittal plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the apparatus's orientation or position.

The indicative line may generate notations in various forms, including a visual alert such as highlighting the angle-indicative line, an audio alert such as providing a continuous sound with variable frequency indicative of the proximity between the current angle and the desired angle, and a small vibration that allows the user to notice the angular change. It should be appreciated that any audio alert may be used, such as a single sound or series of sounds when the desired angle is reached. Likewise, a single vibration or a series of vibrations may be emitted when the desired angle is reached. In some implementations, the flow chart 500 illustrated in FIG. 5B may be applicable for generating indication angles in the transverse plane or the coronal plane for indicating a respective transverse angle or a coronal angle.

Figure 5C:
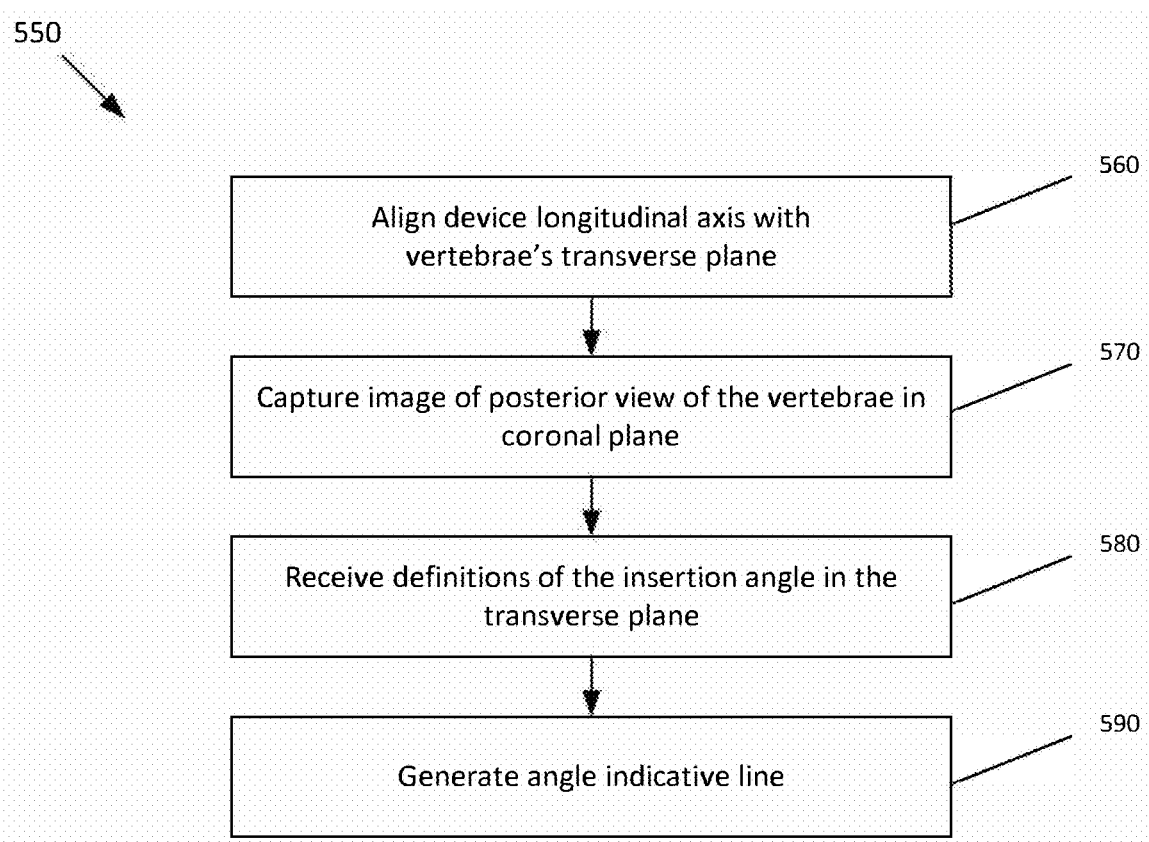

FIG. 5C illustrates a flow chart 550 of an implementation for indicating a transverse angle, which is an angle with respect to the transverse plane of the vertebra. The method of the flowchart 550 is for verifying any pedicle screw insertion angle in the transverse plane of the vertebra 205. At 560, the axis 305 of the apparatus 300 is aligned with the transverse plane. In some embodiments, a user may hold the apparatus 300 and rotate the apparatus 300 to match a marking indicating the axis 305 with features of the vertebra 205 that indicate the transverse plane. In some embodiments, the marking may be displayed on the screen as the user aligns the device.

At 570, the image of the posterior view is captured in the coronal plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 580, definitions of the insertion angle in the transverse plane 130, and the initial position 375 of the pilot hole are provided by a user, as similar to the sagittal angle defined at 530.

At 590, an angle-indicative line for the corresponding transverse angle is generated by a processor and displayed on the display 360. The angle-indicative line can rotate in response to the apparatus 300 rotation and provides a notification when the apparatus 300 approximately forms the insertion transverse angle, as defined in step 580, between the apparatus 300 longitudinal axis 305 and the transverse plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the apparatus's orientation or position.

Figure 5D:
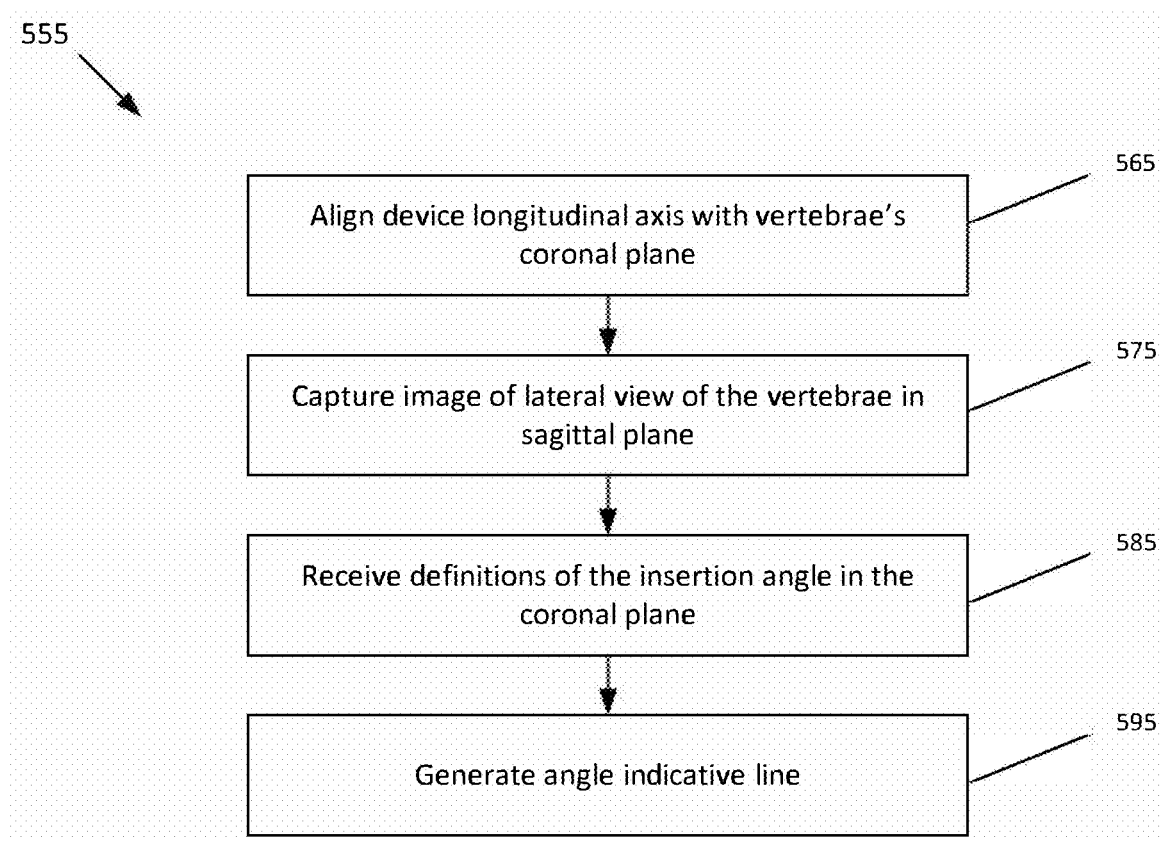

FIG. 5D illustrates a flow chart 555 of another implementation for indicating a coronal angle. The method of the flowchart 555 is for verifying any insertion angle of a pedicle screw 210 in the vertebra 205 in the coronal plane 120. At 565, the axis 305 of the apparatus 300 is aligned with the coronal plane. In some embodiments, a user may hold the apparatus 300 and rotate the apparatus 300 to match a marking indicating the axis 305 with features of the vertebra 205 that indicate the coronal plane. In some embodiments, the marking may be displayed on the screen as the user aligns the device.

At 575, the image of the lateral view is captured in the sagittal plane. In one embodiment, the apparatus 300 includes a smart phone, a tablet computer, a laptop computer, or any portable computational device including those that include a camera for capturing a representation of the posterior view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 585, respective definitions of the insertion angle in the coronal plane 120, and the initial position 375 of the pilot hole are provided by a user, as similar to the sagittal angle defined at 530.

At 595, an angle-indicative line for one of the corresponding coronal angle is generated by a processor and displayed on the display 360. The angle-indicative line can rotate in response to the apparatus 300 rotation and provides a notification when the apparatus 300 approximately forms the insertion coronal angle between the apparatus 300 longitudinal axis 305 and the coronal plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the apparatus's orientation or position.

Figure 6A:
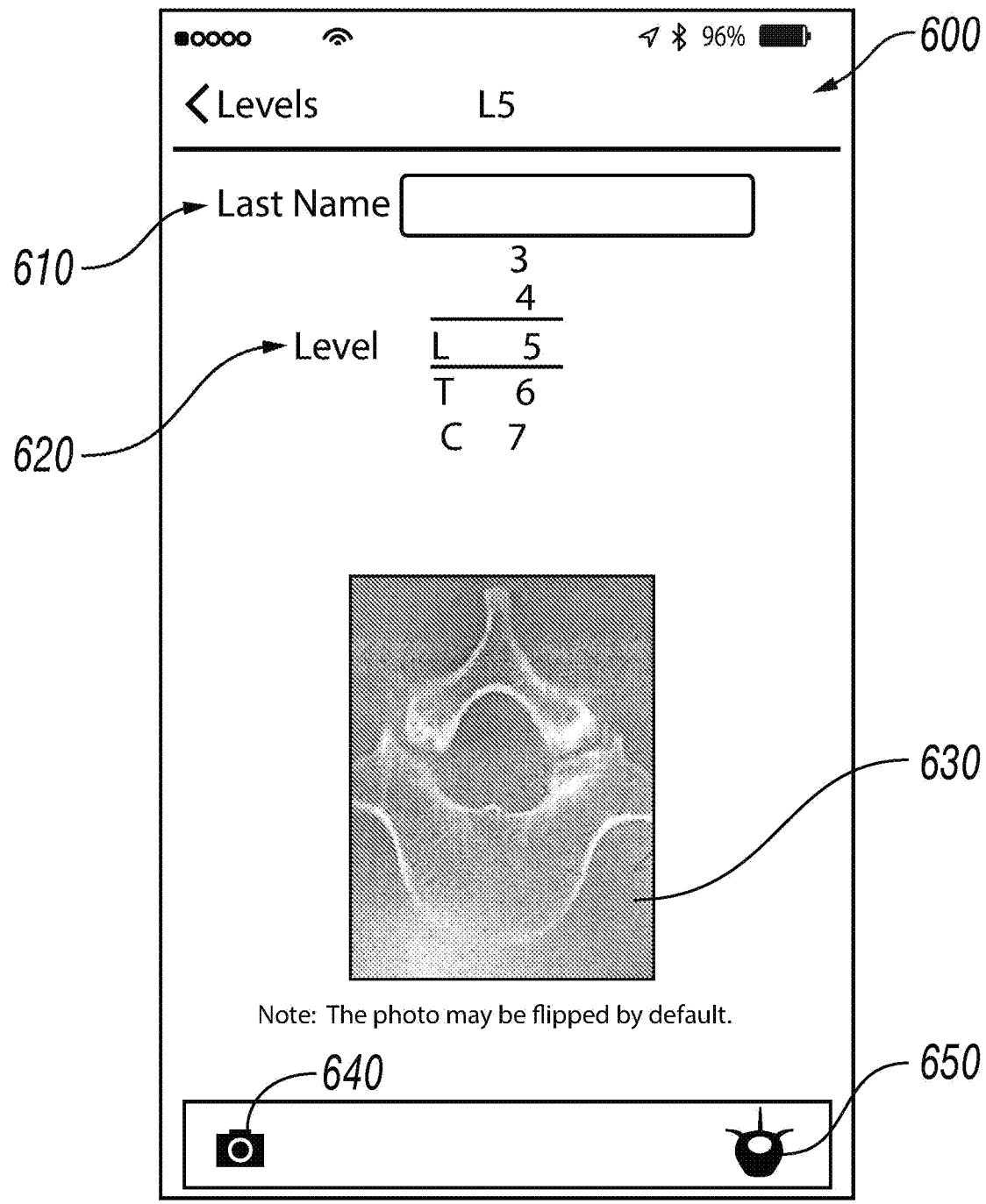
Figure 6B:
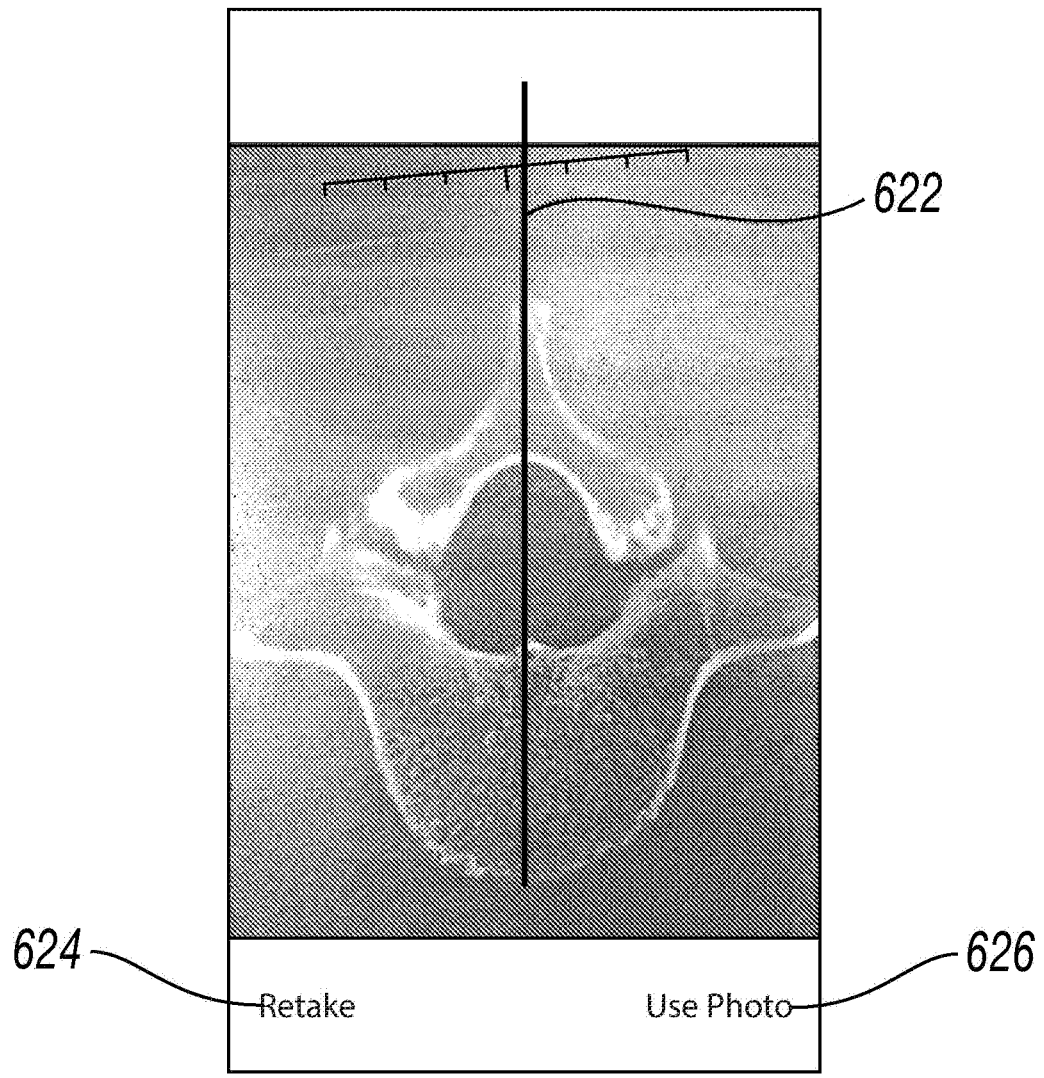
Figure 6C:
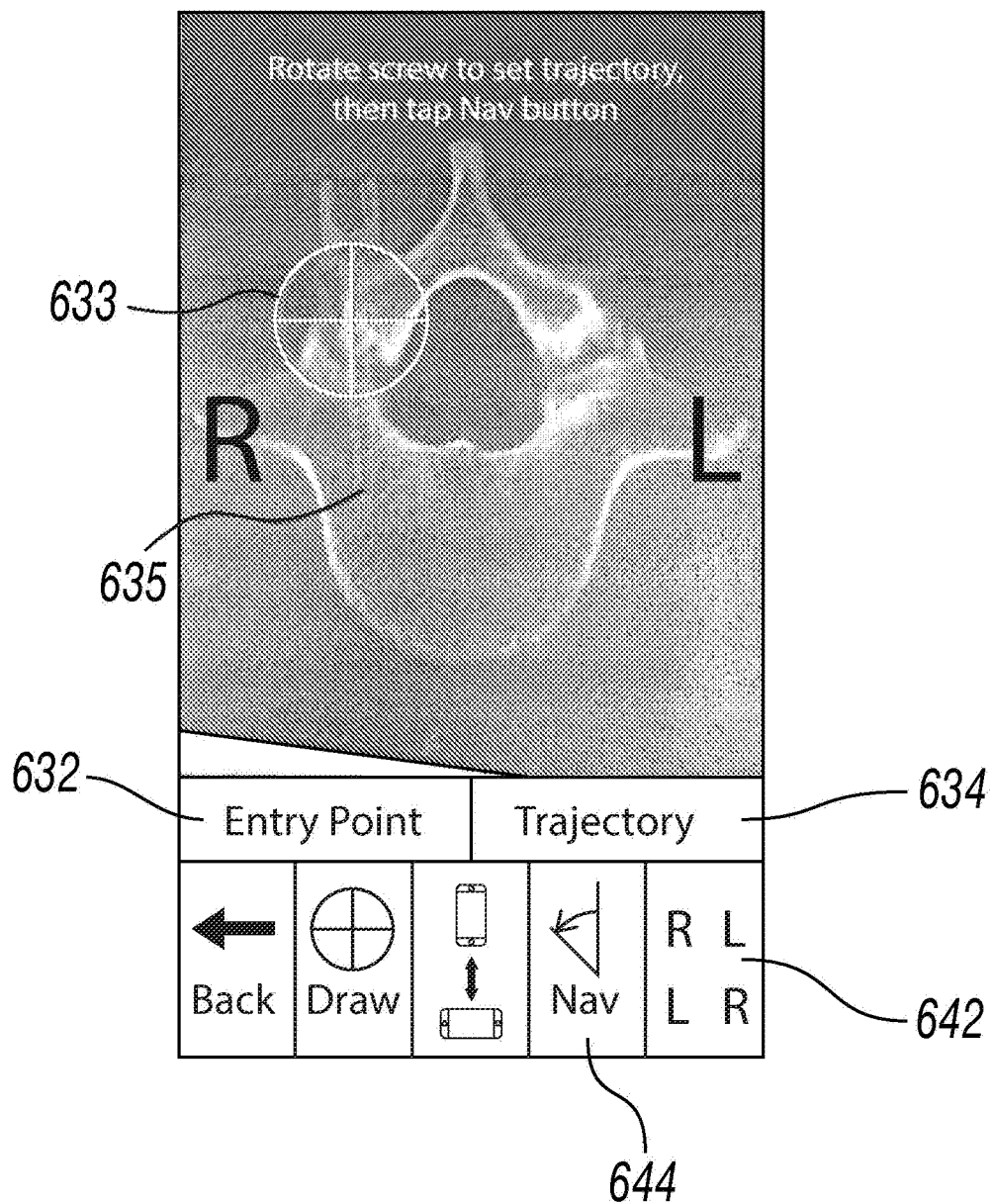
Figure 6D:
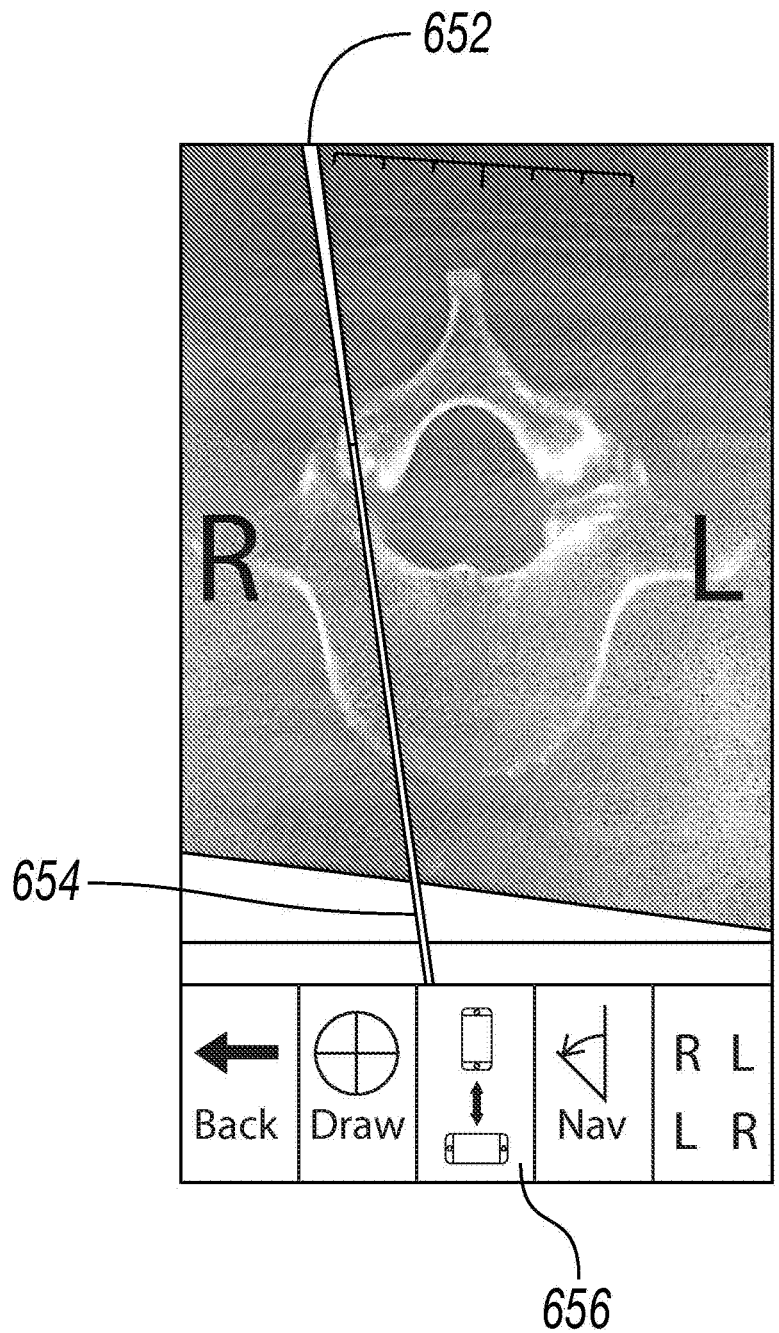

FIGS. 6A-6D illustrate examples of user interfaces for controlling a computer implemented program to perform the methods shown in FIG. 5A-5D. FIG. 6A illustrates an interface 600 for selecting vertebra of a patient, FIG. 6B illustrates aligning the axis 305 of the apparatus 300 with the sagittal plane, FIG. 6C illustrates defining a pedicle screw's position and its sagittal angle 370, and FIG. 6D illustrates generating an angle-indicative line 652 for showing the angle between the longitudinal axis of the apparatus and the sagittal plane. In some embodiments, the angle-indicative line may represent a virtual gearshift probe, or other instrument for aligning a pedicle screw or pilot hole. Where the virtual gearshift is properly aligned, the virtual gearshift may change colors, or may change length or width. The angle-indicative line can rotate in response to the apparatus 300 rotation and provides a notification when the apparatus 300 approximately forms the insertion coronal angle between the apparatus 300 longitudinal axis 305 and the coronal plane.

In FIG. 6A, the patient's profile may be selected or added by typing the last name of the patient in the window 610. The corresponding vertebra for the desired angle is selected in the window 620. The camera button 640 allows a user to take a picture of the vertebra. The picture is then shown in the window 630. The button 650 allows the user to move onto the next step. As previously discussed, the picture at the vertebra may be provided without use of the camera or camera button 640.

For example, by using a camera of a mobile device, a user can take a picture of an axial view (either CT or MM) in the transverse plane 130, of the desired vertebral body 205. Use the red line 622 to line up the vertebral body so that it is proximately vertical for aligning with the sagittal plane (or other desired plane), as shown in FIG. 6B. A retake button 624 allows the user to go back to the previous steps to retake the image to ensure the alignment is proper. The button 626 allows the user to select the current photo to be used in the following operations.

After selecting button 626, the user may be returned to the detail view as shown in FIG. 6C. The photo may, in some embodiments, be automatically flipped to approximate its position during surgery. Button 642 may be selected to flip the orientation of the photo. For example, the RL button 642 can be used to flip the picture (and pedicle screw) depending on whether the surgeon is placing the screw while looking towards the patient's head or towards their feet.

The user next selects the optimal pedicle screw position by selecting the navigation button 644 and by moving the crosshairs 633 to the cortical entry point of the screw, then tapping the trajectory button 634 and rotate the screw to its desired position 635.

Tap the Nav button 644 and a virtual gearshift probe 652 appears on the screen. The gearshift probe's orientation matches the orientation of the apparatus 300. In some embodiments, once the angle of the gearshift probe 652 is about 20 degrees within the selected trajectory, the gearshift probe 652 will turn yellow, at 5 degrees, it will turn green, and when the alignment is within 1 degree of the target angle, a green line 654 will extend outward and the pedicle screw will disappear.

In some embodiments, the device or apparatus 300 can be placed in a sterile bag and then be placed against the gearshift probe as it is being used to create the path for the pedicle screw.

Some gearshift probes may be too short to allow the device (apparatus 300) to be placed against them lengthwise. If this is the case, tap the 90 degree button 656 and the screen will be rotated so the short edge of the device can be placed against the gearshift probe.

Other implementations of the disclosed system and method are possible. For example, the apparatus 300 may also use a second or more views to define various angles not limited within the sagittal plane. For example and in accordance with the foregoing disclosure, images may be captured from the superior, lateral, posterior, anterior views, and various combinations thereof, to provide multiple reference points so that three-dimensional representations of the alignment angles can be presented.

In addition, different mobile computer devices may be used or modified into the apparatus 300 by equipping corresponding image acquisition units, input terminals, and motion or orientation sensing units. In some embodiments, the apparatus 300 includes a smart phone or another electronic device having a gyroscope. In addition, other motion or orientation sensors may be included such as the inertial measurement unit 334, and the accelerometers 336. The apparatus 300 may also be attached onto various medical devices or equipment for guiding insertion angles that require high precision and ease of use. The smartphone may be an iPhone for example. Also, in some application, the mobile computer device may be an iPod Touch, iPad, Android phone, Android tablet, Windows Phone, Windows tablet, or Blackberry phone. Also, in some applications, the mobile computer device may be an Apple TV in combination with an Apple TV remote, or a Nintendo Wii in combination with a Nintendo Wii remote. Indeed, the mobile computer device may be any combination of electronic devices where the orientation sensor (such as a gyroscope) is in one electronic device and the processor is in another electronic device.

In some embodiments, axis other than the device's longitudinal axis may be used. Axes can be defined by a portion of the device (e.g., an edge or surface of the device). More than one orientation apparatus 330 may be used at the same time to give a three-dimensional viewing. Surgical apparatus may include pedicle screws, gearshift probes, and other medical devices.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:

1. A method for assisting with orienting a medical device at a desired location, the method comprising:
displaying, on an electronic device, by one or more processors, an image of a representation of a location at or adjacent the desired location;
simulating, by one or more processors, a position of the medical device relative to the image to determine a first desired orientation of the medical device relative to a plane of the image;
positioning the medical device at or adjacent the desired location;
positioning the electronic device at a reference position relative to the medical device;
determining, by one or more processors, an orientation of the electronic device using an orientation sensor; and
determining, by one or more processors, when the orientation of the electronic device is positioned at or about the first desired orientation of the medical device relative to the plane of the image.

2. The method of claim 1, further comprising:
determining, by one or more processors, when the electronic device is positioned at or about a second desired orientation of the medical device relative to a second plane of a second image; and
outputting a notification when the electronic device is positioned at or about the first desired orientation and the second desired orientation.

3. The method of claim 1, wherein the image is a superior view of the desired location, a lateral view of the desired location, or a posterior view of the desired location.

4. The method of claim 1, wherein the image is a pictorial view, an x-ray, a radiograph, a computed tomography scan, or a magnetic resonance image.

5. The method of claim 1, wherein the plane is one of an axial plane, a coronal plane, or a sagittal plane.

6. The method of claim 1, wherein the medical device is a pedicle screw, a steel rod, a stent, an interbody cage, a bone graft, an implant, a gearshift probe, a drill guide, or a drill bit.

7. The method of claim 1, wherein the image includes a representation of at least one or more portions of a body from a group that includes a spine, a joint, a rib cage, a cranium, an artery, a lung, or other portion of the body to receive an implant.

8. The method of claim 1, wherein the electronic device includes two or more computing devices that include one or more processors.

9. The method of claim 1, further comprising creating an opening in a body part for receiving the medical device using an instrument positioned adjacent to the electronic device.

10. The method of claim 1, wherein the orientation sensor comprises at least one or more of a gyroscope, an accelerometer, or an inertial measurement unit.

11. The method of claim 9, wherein the instrument is one of a gearshift probe, a drill guide, or a drill bit.

12. The method of claim 1, wherein determining the orientation of the electronic device is determined with respect to an orientation of a longitudinal axis of the electronic device.

13. A method for assisting with orienting a medical device at a desired location, the method comprising:
receiving, by one or more processors, a first input from a user specifying a first positioning angle of the medical device in a first image of a representation of a location at or adjacent the desired location;
receiving, by one or more processors, a second input from the user specifying a second positioning angle of the medical device in a second image of the representation of the location at or adjacent the desired location, the second image orthogonal to the first image;
determining, by one or more processors, a three-dimensional orientation of an electronic device for positioning the medical device based on the first positioning angle and the second positioning angle; and
displaying, by one or more processors, a visual indicia on a display device that represents the three-dimensional orientation of the medical device.

14. The method of claim 13, wherein the electronic device and the display device use one or more processors.

15. The method of claim 13, wherein the display device and the electronic device are included in a device.

16. The method of claim 13, wherein the first positioning angle corresponds with a first axis of the medical device and the second positioning angle corresponds with a second axis of the medical device.

17. The method of claim 13, wherein the first positioning angle corresponds with a first axis of an instrument and the second positioning angle corresponds with a second axis of the instrument.

18. The method of claim 13, wherein the first image is an axial view, and the second image is a lateral view.

19. The method of claim 13, wherein the medical device is a pedicle screw, a steel rod, a stent, an interbody cage, a bone graft, an implant, a gearshift probe, a drill guide, or a drill bit.

20. The method of claim 13, wherein the first image and the second image include representations of at least one or more portions of a body from a group that includes a spine, a joint, a rib cage, a cranium, an artery, a lung, or other portion of the body to receive an implant.

21. The method of claim 13, wherein the electronic device includes two or more computing devices that include one or more processors.

* * * * *